United States Patent [19]

Beavin

[11] Patent Number: 5,495,568
[45] Date of Patent: Feb. 27, 1996

[54] COMPUTERIZED CLOTHING DESIGNER

[76] Inventor: William C. Beavin, 5527 Waterman #2E, St. Louis, Mo. 63112

[21] Appl. No.: 175,780

[22] Filed: Dec. 27, 1993

Related U.S. Application Data

[63] Continuation-in-part of Ser. No. 801,914, Dec. 3, 1991, Pat. No. 5,273,038, which is a continuation-in-part of Ser. No. 550,343, Jul. 9, 1990, abandoned.

[51] Int. Cl.$^6$ ..................................................... G06F 17/50
[52] U.S. Cl. ......................... 395/161; 395/119; 395/152; 395/125
[58] Field of Search .................................... 395/125, 126, 395/127, 128, 129, 130, 131, 155, 161, 141, 119, 152; 364/188, 468, 469, 470; 382/1, 8, 41; 345/122

[56] References Cited

U.S. PATENT DOCUMENTS

| | | | |
|---|---|---|---|
| 4,539,585 | 9/1985 | Spackova et al. | 382/41 |
| 4,888,713 | 12/1989 | Falk | 395/125 |
| 4,916,634 | 4/1990 | Collins et al. | 364/470 X |
| 4,936,135 | 6/1990 | Annis et al. | 73/7 |
| 4,949,286 | 8/1990 | Ohba | 395/125 |
| 5,163,006 | 11/1992 | Deziel | 364/470 |
| 5,163,007 | 11/1992 | Slilaty | 364/470 |
| 5,267,154 | 11/1993 | Takeuchi et al. | 395/119 X |

Primary Examiner—Raymond J. Bayerl
Assistant Examiner—Crescelle N. dela Torre
Attorney, Agent, or Firm—Henry W. Cummings

[57] ABSTRACT

A computer system receives data describing fabric characteristics such as weave pattern, frictional characteristics, average fibers per strand, strand wear characteristics, and elasticity. Fabric colors and patterns are also inputs. Data describing an individual's physical characteristics such as dimensions and complexion are input into the computer system's memory. Digitized photographs of an individual may be mapped over a three dimensional image tailored to that individual's dimensions. Garment models are placed over the three dimensional images, which reflect the inputted fabric characteristics and color patterns. The fit is tailored to match the three dimensional model, and shown graphically on the computer display device. The three dimensional model moves as the individual would move, such as raising the arms, bending, walking, or running. Motion inputs may come from prerecorded maneuver data, or user input through such means as computer keyboard, mouse, joystick, or other interaction devices such as body position sensors worn by the user to accurately input individual range of motion data. Friction between the individual and the fabric is monitored, as well as between areas of fabric rubbing on fabric, and shown graphically as a hot spot. User interaction to adjust the garment dimensions can be applied to adjust for the binding. The fabric model is affected by the motion through stretching and friction. Fabric conditions, such as temperature, moisture content, foreign objects, and fabric defects can be modified, and the fabric model indicating that fabric's response may be observed as the three dimensional model moves through normal ranges of motion. Fabric characteristics such as color and pattern may be modified dynamically, so that the user may observe different garments. The three dimensional model can be made to move in slow motion, real-time, or faster than real-time to observe results. After the user is satisfied with the garment design, it is stored in computer memory, and can be presented in the form of a printed pattern to be placed over the chosen fabric and assembled into an actual garment, or a set of control outputs to an automated cutting machine may directly control cutting the garment's required pieces of fabric to construct the accurately tailored garment.

10 Claims, 6 Drawing Sheets

COMPUTERIZED CLOTHING DESIGNER

REFERENCE TO RELATED APPLICATION

This application is a continuation-in-part of application Ser. No. 801,914 filed Dec. 3, 1991, now U.S. Pat. No. 5,273,038, which in turn is a continuation in part of Ser. No. 550,343, filed Jul. 9, 1990, now abandoned.

BACKGROUND OF THE INVENTION

U.S. Pat. No. 4,984,181 discloses the means to display the resulting pattern's and colors of a piece of fabric based on yarn strand color patterns and weave methods, addressing only the resultant fabric appearance.

OBJECTS OF THE INVENTION

One object of the invention is to combine fabric characteristic models with individual subject characteristic models using various garment configurations, and display to the observer a three dimensional interactive image of the garment as worn by the individual.

Another object is the ability to graphically display effects of garment wear, such as areas of high friction and excessive wear.

Another object is to provide the operator with the ability to manipulate fabric characteristics, the individual's three dimensional model, and garment configurations to tailor the individual's garment.

Another object is the ability to observe the garment's response to full range of motion activities by causing the individual's three dimensional model to move when overlaid with the garment being studied.

Another object is the ability to output a garment pattern for cutting fabric to match the computer designed garment for a particular individual.

Another object is to utilize control signals outputted directly to cutting tools to cut the fabric.

SUMMARY OF THE INVENTION

A computer system receives data describing fabric characteristics such as weave pattern, frictional characteristics, average fibers per strand, strand wear characteristics, and elasticity. Fabric colors and patterns are also inputs. Data describing an individual's physical characteristics such as dimensions and complexion are input into the computer system's memory. Digitized photographs of an individual may be mapped over a three dimensional image tailored to that individual's dimensions. Garment models may be placed over the three dimensional images, which reflect the inputted fabric characteristics and color patterns. The fit of this garment is tailored to match the three dimensional model, and shown graphically on the computer display device. To ensure proper fit, the three dimensional model moves as the individual would move, such as raising the arms, bending, walking, or running. Motion inputs may come from prerecorded maneuver data, or user input through such means as computer keyboard, mouse, joystick, or other interaction devices such as body position sensors worn by the user to accurately input individual range of motion data. Friction between the individual and the fabric is monitored, as well as between areas of fabric rubbing on fabric. Friction is shown graphically as a hot spot, and user interaction through mouse, keyboard, or the pointing device to adjust the garment dimensions can then be applied to adjust for the binding. The fabric model itself is affected by the motion through stretching and friction, and based on input fiber characteristics, the fibers stretch and break. Fabric conditions, such as temperature, moisture content, foreign objects, and fabric defects can be modified, and the fabric model indicating that fabric's response may be observed as the three dimensional model moves through normal ranges of motion. Fabric characteristics such as color and pattern may be modified dynamically, so that the user may observe different garments. The three dimensional model can be made to move in slow motion, real-time, or faster than real-time to observe results. Slow motion can be used to analyze such things as a garment's reaction through a particular motion. Real-time is used to show the garment during normal usage. Faster than real-time shows projected garment responses throughout it's lifespan, including failure points and overstressed areas. After the user is satisfied with the garment design, it is stored in computer memory, and can be presented to the user in the form of a printed pattern to be placed over the chosen fabric and assembled into an actual garment, or a set of control outputs to an automated cutting machine may directly control cutting the garment's required pieces of fabric to construct the accurately tailored garment.

THE DRAWINGS

SUMMARY OF OPERATION

Figure 1:
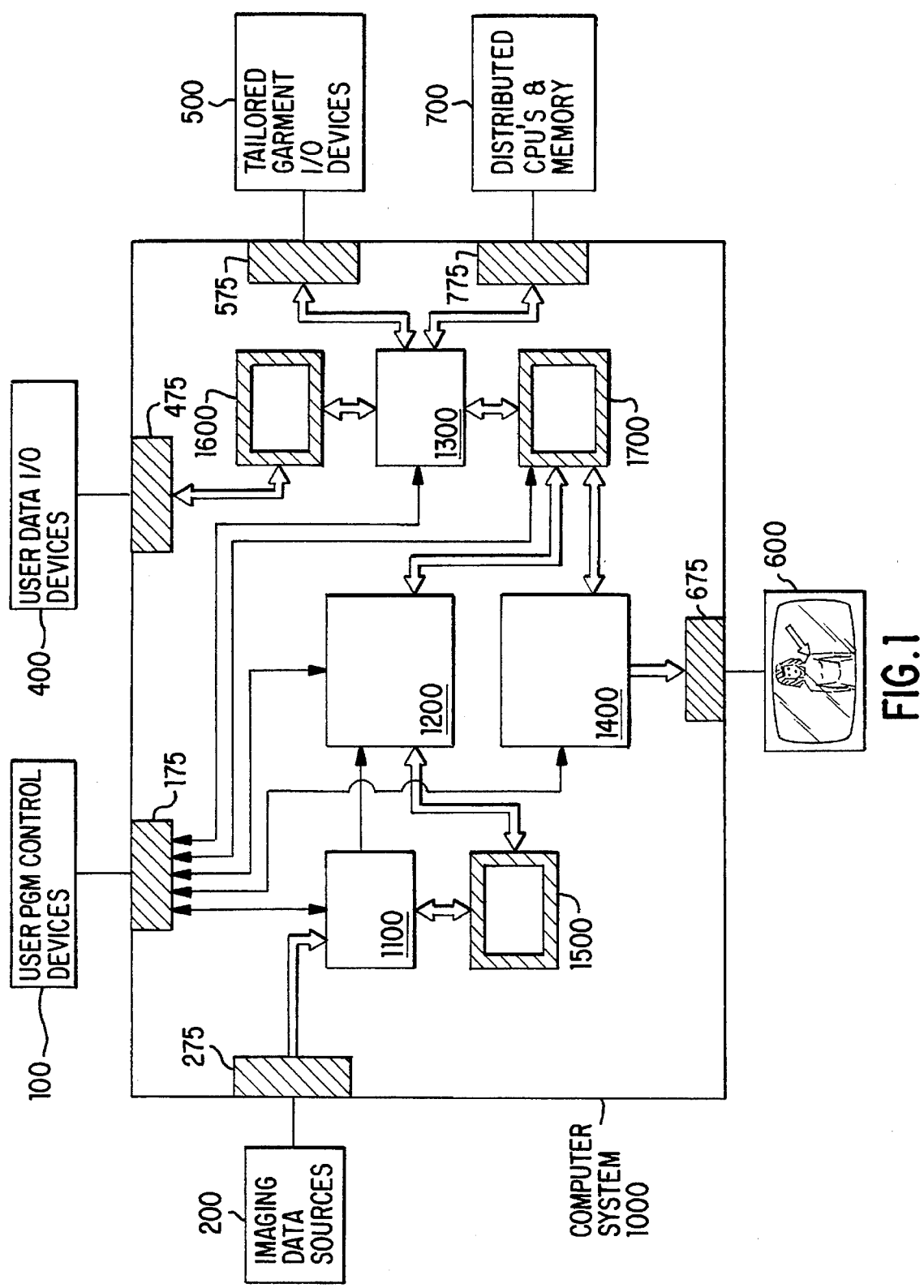
FIG. 1 is a schematic representation of the computerized clothing designer in the present invention.

FIG. 1 is a block diagram of the overall system. Six major features are described.

One feature is the user interactive devices (100) for user control data, which may be such devices as a keyboard, mouse, display terminal, light pen, button/dial box, touch screen, voice I/O, or printing devices.

Another feature is the imaging data (200), which may come from personal or generic dimensional databases, fabric characteristics databases, digitized images, and three dimensional image databases. These databases may come directly from digital media such as computer disks, computer tape, compact disk, or over communications link to computer networks containing such data.

Another feature is the user interaction devices (400), which provide user interaction data to and from devices such as data gloves, data suits, control boxes, position sensors, force sensors, voice systems, touch screens, or other device providing user interaction data.

Another feature is the output device (600), such as a cathode ray tube, projection device, or helmet mounted display.

Another feature is the tailored garment I/O devices (700), such as a printing device or link to automated garment manufacturing devices.

Another feature is the Graphics Image Generator Computer System (1000). Within this computer system, which may be composed of distributed computers through network (700) and connection (775), several computer programs (1100), (1200), (1300), and (1400) run, accessing several blocks of memory (1500), (1600), (1700). These utilize the described input and output means to graphically display a three dimensional object that reflects input activity and can be manipulated by the user.

DETAILED DESCRIPTION OF PREFERRED EMBODIMENT

Figure 2:
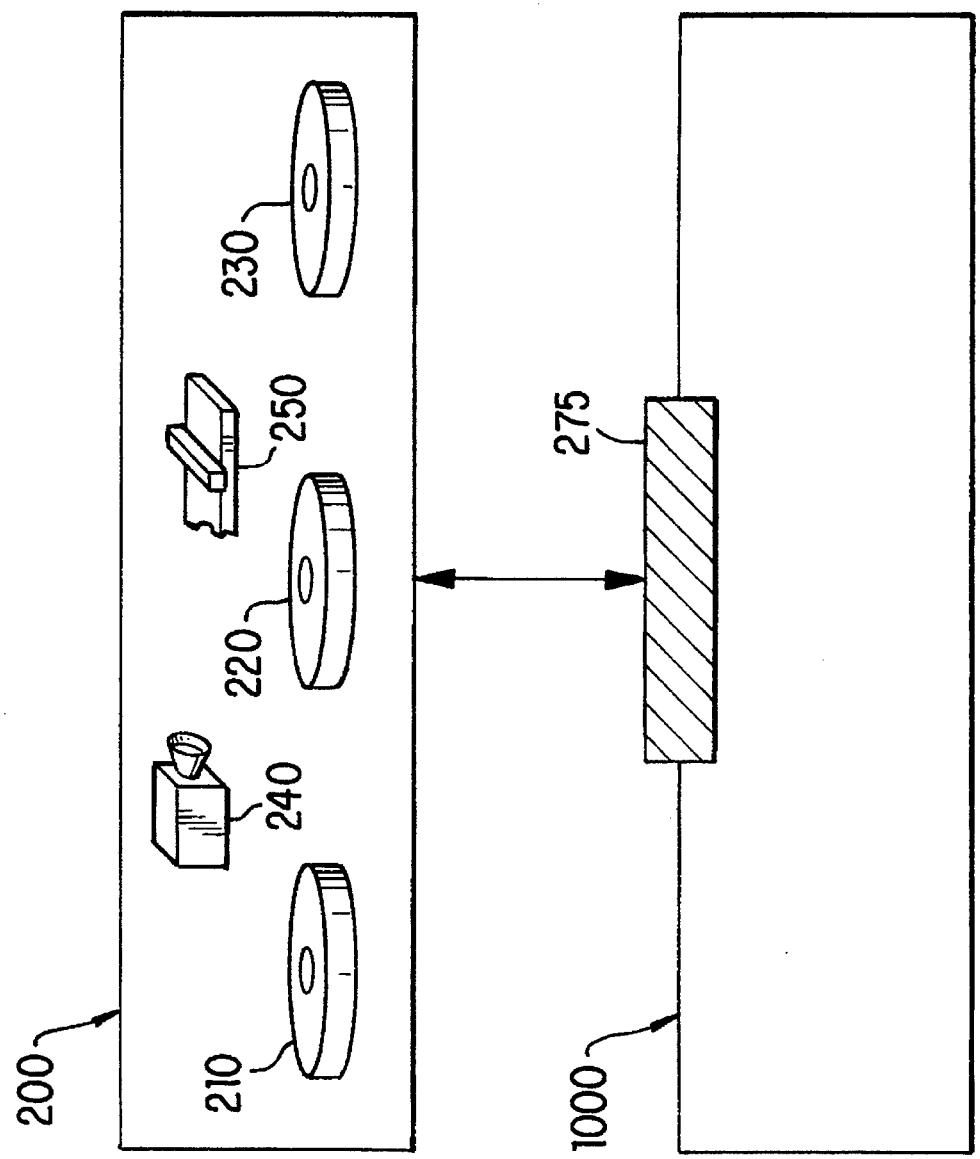
FIG. 2 is a schematic representation of imaging data sources in the present invention.

In accordance with the present invention, a database containing imaging data (200), as shown in FIG. 2, among which are garment three dimensional data (210), fabric data (220), and subject three dimensional data (230), is input to the graphics image generator computer system (1000), as shown in FIG. 1, through data I/O devices (275) such as tape drives, disk drives, or communications ports. Also input are digitized video images (240) and digitally scanned photographs (250) for application to the graphical images.

A three dimensional volume rendering program (1100) such as "Voxel View", which reads data (200) into memory (1500) is activated in the graphics image generator computer system (1000). "Voxel View" is a Registered Trademark of Vital Images, Inc., at P.O. Box 551, Fairfield, Iowa 52556, (515) 472-7726. The preferred embodiments of the graphics image generator computer system (1000) is the Onyx-2 Reality Engine 2 from Silicon Graphics Inc., of Shoreline Blvd., P.O. Box 7311, Mountain View, Calif. 94037-2011.

Several methods are available to map the digitized video images (240) and digitally scanned photographs (250) onto the surface of the three dimensional image data stored in memory (1500), such as "PowerScene", available from Cambridge Research Associates, 1430 Springhill Road, Suite 200, McLean, Va., 22102, (703)790-0505, FAX (703) 790-0370, and a Silicon Graphics provided graphics package call "Performer". One or both of these programs (1200) would access memory (1500), and create resultant data in memory (1700) ready for display generation and user interaction through model dynamics program (1300) and graphics program (1400).

Figure 3:
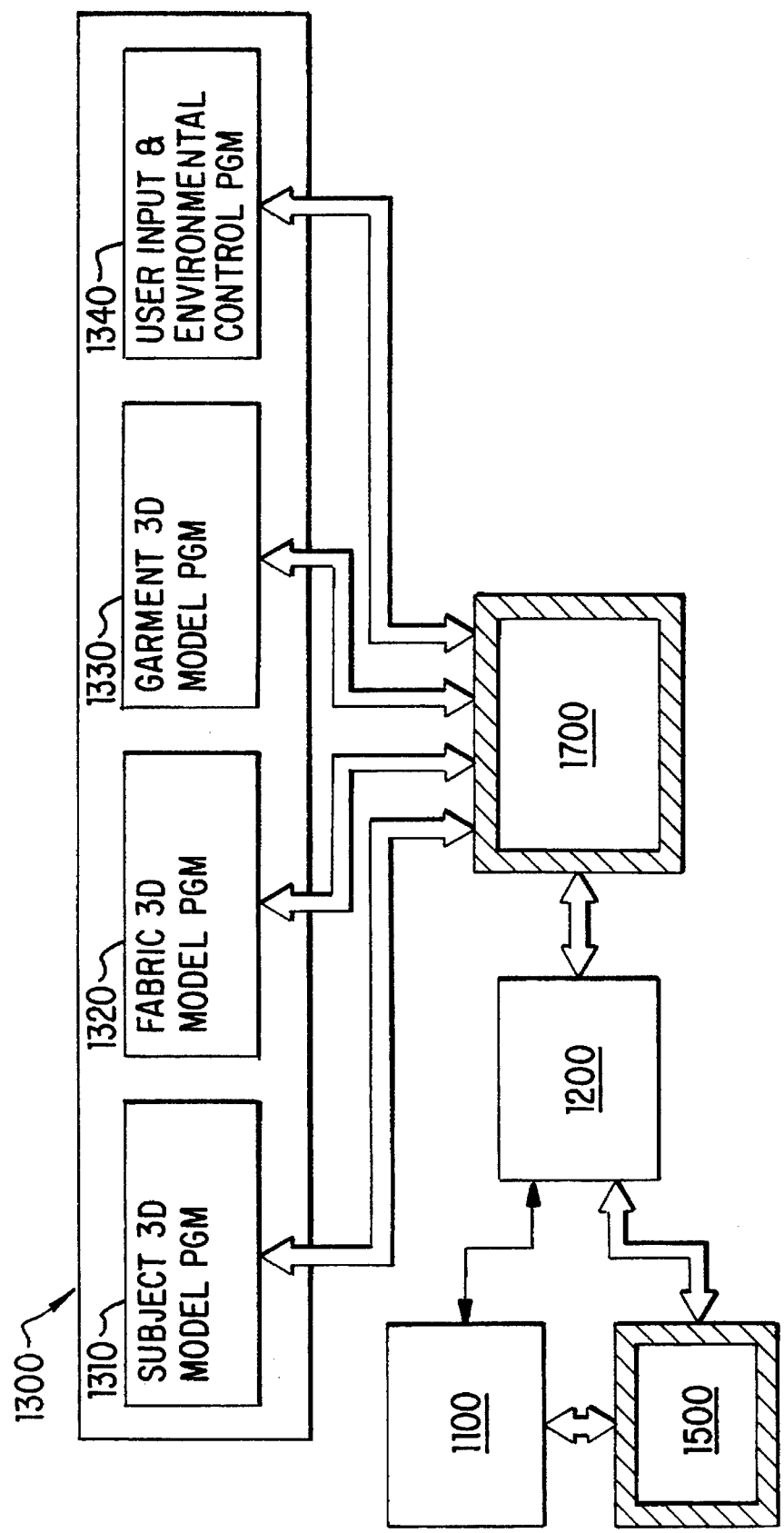
FIG. 3 is a schematic representation of model dynamics programs in the present invention.

The model dynamics programs (1300), as shown in FIG. 3, include the subject three-dimensional model program (1310), fabric three-dimensional model program (1320), garment three-dimensional model program (1330), and user input and environmental control program (1340). These programs read from and write to memory (1700) containing local storage data and three dimensional graphics image data initially deposited by the image generation programs (1100) and (1200).

The model dynamics programs (1300) may run locally on the graphics image generator computer system (1000), or be distributed across other available processors (700) over processor link (775).

The model dynamics programs (1300) produces output (600) suitable for printing, such as in standard post-script printer format, or control sequences suitable to instruct automated cutting, or automated assembly devices.

Fundamental operation of the subject three-dimensional model program (1310) comprises application of the basic graphics model manipulation functions of scaling, rotating, and translating the database three dimensional points contained in memory (1700) for the subject model data to rotate limbs and move about. Preferably motion will reflect user motion data provided by user data devices (400). Skin flexibility and motion results from common techniques such as summation of forces acting upon each three-dimensional point, including skin elasticity, surface compression, and external forces such as that from external garments, and adjusting the location of each point in each of the three dimensions to zero the sum of the forces. Friction on the body surface is calculated based on surface coefficients of friction, normal surface forces, and motion between surfaces.

Figure 5:
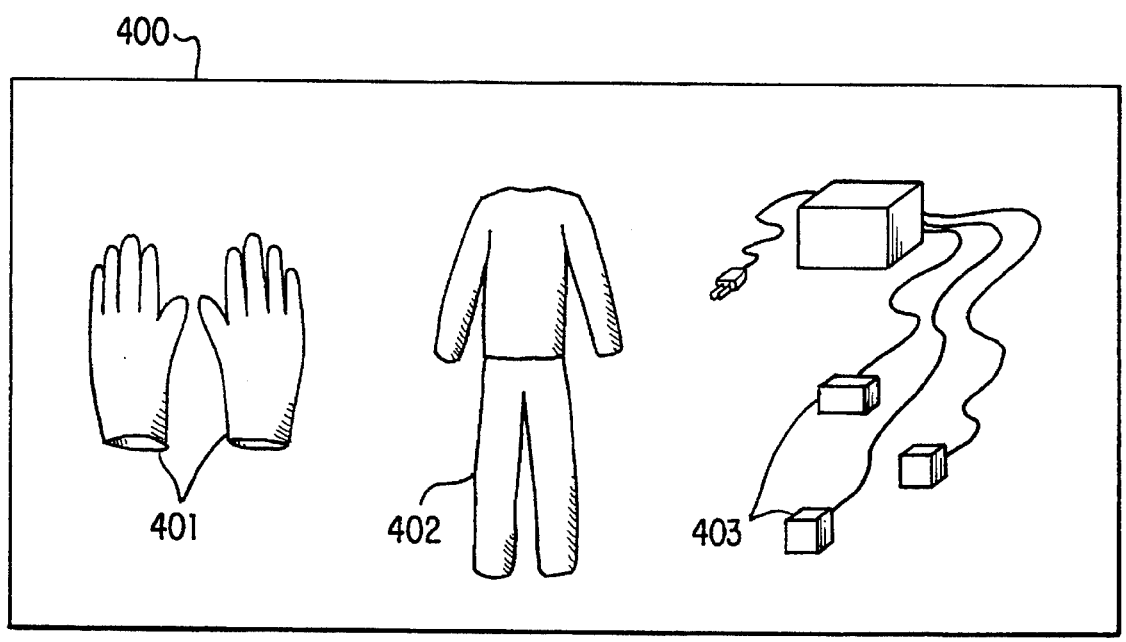
FIG. 5 is a schematic representation of user data Input/Output (I/O) devices in the present invention.
Figure 6:
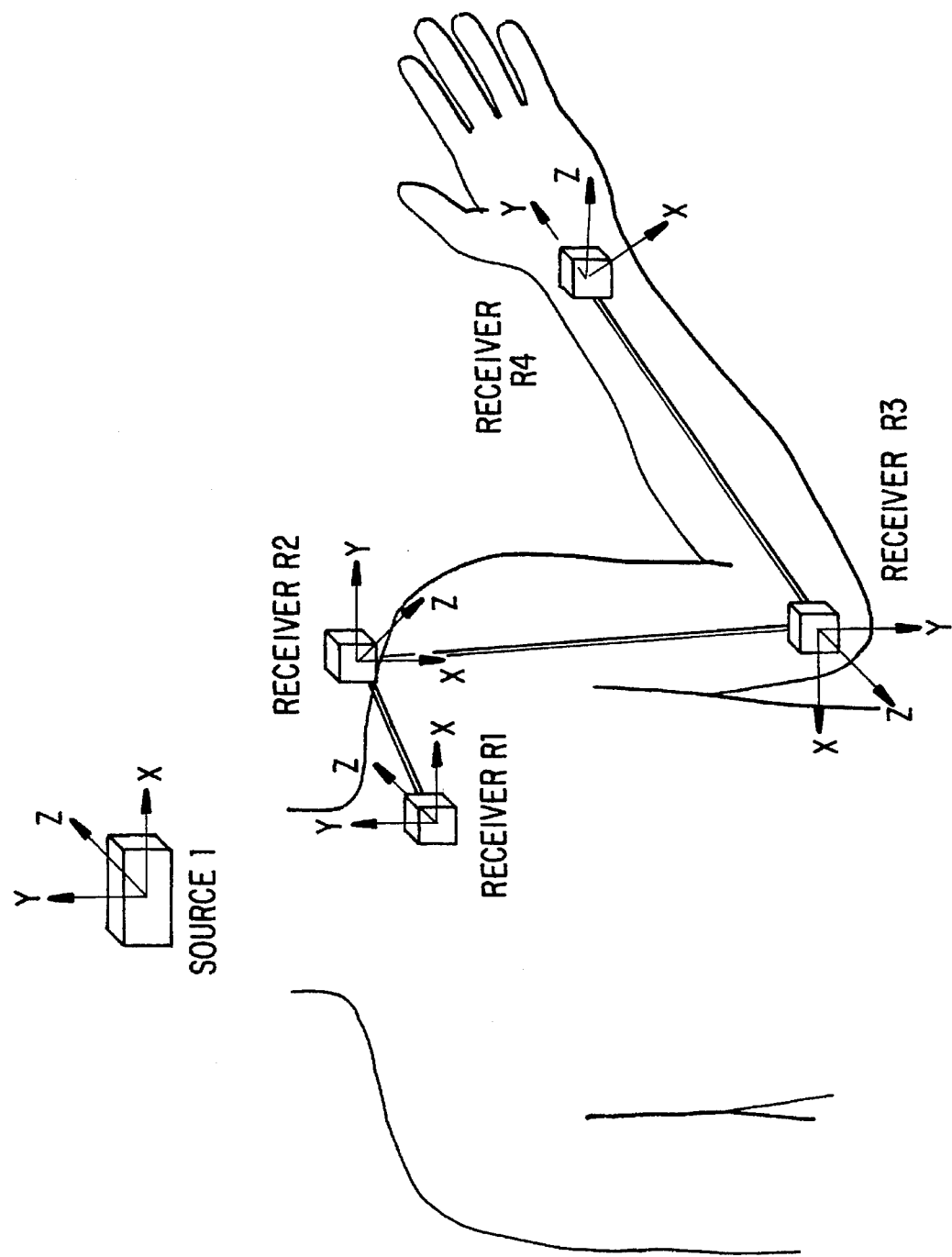
FIG. 6 is a schematic representation of body position sensor locations to obtain user arm motion data.

As an example, position and orientation sensors (403), such as the Polhemus Tracking System, available from Polhemus, Inc. of Colchester, Vt., (802)655-3159, are placed as shown at key locations on the subject's body, as shown in FIG. 5. The subject three-dimensional model program (1310) responds to the user motion data inputted through user data device link (475), and reflects motion of the subject's arm. Positioning of the four sensors could be at the top of the shoulder blade (Receiver R1), the end of the collar bone (Receiver R2), the back of the elbow (Receiver R3), and the back of the wrist (Receiver R4) to provide basic positional inputs of the arm. Each of the Receivers reports its position and orientation relative to a three dimensional coordinate system centered at the Polhemus Tracking System Source unit. The system can be configured to be reported in inches of displacement of the Receiving units from the center of the X, Y, Z axes centered in the Source unit. Orientation can be reported in degrees rotation about the X, Y, Z axes after translating the axes from the Source to the Receiver. Given the four Receiver's positions and orientations, relative positions and angles between each of the receivers can be obtained. The rotation applied at Receiver R1 towards Receiver R2 can be calculated by the formulas:

$$Y_{rotation}=arctan(Z_{delta}/X_{delta})\ Z_{rotation}=arctan(Y_{delta}/X_{delta})\ X_{rotation}=arctan(Y_{delta}/Z_{delta})$$

Applying these rotations at the model location corresponding to the position of R1 will cause the shoulder blade to be drawn with an orientation and position that reflects the actual subject providing the motion inputs. Next, applying the same equations with the position deltas between Receiver R3 and Receiver R2 to calculate rotations to be applied at the position of R2, and drawing at that point with the applied relative rotations the upper arm member of the subject being modelled will cause the upper arm to reflect the proper upper arm orientation. Obtaining the rotations similarly from Receiver R3 to Receiver R4, applying them at the position of R3, and then drawing the forearm section with the applied relative rotations will cause the forearm to reflect the proper forearm orientation. Using the technique well known to graphics programmers of pushing and popping rotational matrices on the matrix stack, several members can be rotated relative to a common base, such as the fingers of the hand, all of which inherit the basic orientation of the hand.

After the basic "rigid" rotations of the subject model members is completed, such as for the basic bone structure movements described above, a summation of forces is performed at each point. Each point seeks equilibrium, at which the sum of all forces in each axis acting upon it are minimal. Equilibrium is approached by translating the point's three dimensional location in the direction of it's force vector, which is the sum of the forces acting upon it.

After the translation, forces are once again summed for each point, and more translations are applied until a prescribed equilibrium is obtained for the overall section undergoing motion. Other means well known to those skilled in computational dynamics could be applied to reflect the motion of each point. These translations reflect the "soft" tissue responses to the inputted motion.

The fabric three-dimensional model program (1320) operates similar to the subject three-dimensional model program (1310) in that motion of each fabric three-dimensional point stored in memory (1700) is applied to minimize the sum of the forces acting on each point. Various techniques for modelling fabric wear could be applied, most notably the case when stretching forces exceeding a particular fiber's strength, causing it to break.

The garment itself is modelled by the garment three-dimensional model program (1330). It contains dimensions for fabric pieces connected to construct the garment from templates, and is combined with the fabric three dimensional model program (1320) to present the garment under consideration. Key items modelled by the garment model are the mapping of fabric pieces and characteristics over the subject model, and friction resulting from the action of the fabric and the underlying model. As stretching forces cause fibers to break, the garment model modifies the fabric description in memory to indicate the loss of the fiber connection, and decrements the average fiber content at the location of the failure. Friction is calculated from standard frictional force equations, such as: friction force=coefficient of friction≠normal force. Normal forces indicate areas of pressure, and can be shown graphically as variations in color. Irritation caused by rubbing can be expressed as a function of frictional force and fabric displacement. Those familiar with work and energy equations will recognize this relationship to resemble the work equation:

$$work = force \neq displacement$$

Therefore, multiplying frictional force by displacement for the current time increment being modelled to yield work performed to move the fabric across the skin surface will give an indication of current irritation. Accumulated irritation can be indicated by summing accumulated work performed at each point modelling the skin surface of the subject being modelled, and shown graphically to the user.

The user input and environmental control program (1340) is the main executive program controlling execution of the programs (1310), (1320), and (1330). As well as synchronizing the programs by distributing a request to start the next motion update time slice, it performs handling of the user input data from user input devices (100), and outputs requested tailored garment data (500) from memory (1700). It controls external factors considered in the modelling program's force equations such as humidity and temperature.

Figure 4:
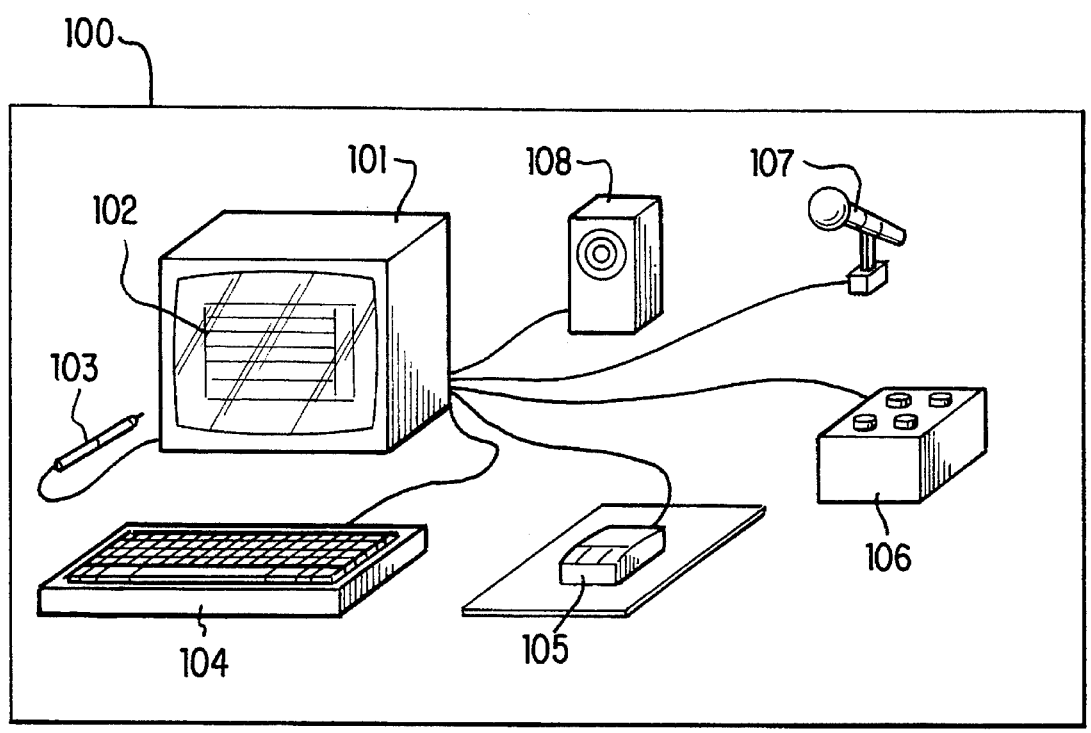
FIG. 4 is a schematic representation of user program control devices in the present invention.

User program control devices (100), shown in FIG. 4, such as terminal (101), touchscreen (102), light pen (103), keyboard (104), mouse or trackball (105), control button/dial box (106), voice recognition (107), voice response (108), or other applicable device, and user data I/O devices (400), shown in FIG. 5, such as data gloves (401), data suit (402), position sensors (403), or other user data source, provide user inputs to the programs (1100), (1200), (1300), (1400), and memory (1700). These inputs provide control for program execution, and data required for interactive functionality.

Three dimensional graphics program (1400) is available through the visualization phases of programs like "VoxelView", "PowerScene", or "Performer", described for use also in data input and manipulation programs (1100) and (1200), tailored with other available programs or user developed programs to produce the resultant image of the garment as worn by the subject on display device (600) through video display connection (675).

What is claimed is:

1. A clothing designer computer system comprising:

means for obtaining physical characteristics directly from a purchaser including physical dimensions;

means for obtaining complexion data directly from said purchaser;

means for obtaining digitized photographic data of said purchaser;

means for generating a three dimensional model of said purchaser;

computer processing means for generating movement of said model through motion contemplated by said purchaser;

means for inputting fabric characteristics of potential fabric materials;

means for inputting frictional characteristics of said fabric materials with said moving model;

means for inputting environmental data conditions including temperature range and moisture content;

means for inputting wear data for said fabric materials into said computer system;

computer processing means for processing said frictional characteristics and said wear data during movement of said model;

computer processing means for determining life span of said fabric materials based on said model movement, said wear data, said frictional characteristics; and said environmental data;

computer processing means for determining appropriate fabric, size, contour of garment for said purchaser; and display means for illustrating movement of said model with said garment in place upon said model.

2. A clothing designer computer system according to claim 1 wherein said physical characteristics include size, weight, length of arms, width of arms, leg lengths, leg widths, bust, and waist.

3. A clothing designer computer system according to claim 1 wherein said fabric characteristics include weave pattern, fibers per strand, elasticity, color and color patterns.

4. A clothing designer computer system according to claim 1 wherein said computer processing means moves said model in slow motion, real time and accelerated time.

5. A clothing designer computer system according to claim 1 wherein said computer system provides control of cutting the fabric to size.

6. A method of designing a computer garment comprising:

providing a clothing designer computer system; supplying to said computer system fabric characteristics of potential fabrics for the garment; supplying to said computer system physical characteristics taken directly from a purchaser; supplying to said computer system complexion data taken directly from said purchaser; supplying digitized photographic data of said purchaser; generating a 3-dimensional model of said purchaser; generating movement of said model through motions contemplated for use of the garment; supplying wear data for said fabrics into said computer system; supplying environmental data including temperature range and moisture content, contemplated for said fabrics; supplying friction data between said fabrics and said physical characteristics of said purchaser; processing said fabrics, said wear data, said frictional data and said environmental data upon said model as said model moves through contemplated purchaser activity; determining the appropriate fabric, contour of garment, and size for said purchaser; and displaying the resulting garment upon said model and movement of said model with said garment in place.

7. A method according to claim 6 including measuring the size, weight, length of arms, width of arms, leg lengths, leg widths, bust and waist.

8. A method according to claim 6 including processing said model through wear and environmental conditions to determine life span of the garment.

9. A method according to claim 6 including processing said model through slow motion, real time and accelerated time.

10. A method according to claim 6 including cutting the fabric to size with said computer system.

* * * * *